United States Patent [19]

Sauer et al.

[11] Patent Number: 5,626,588
[45] Date of Patent: *May 6, 1997

[54] TROCAR WOUND CLOSURE DEVICE

[75] Inventors: Jude S. Sauer, Pittsford; Roger J. Greenwald, Holley; Mark A. Bovard, Palmyra, all of N.Y.

[73] Assignee: LaserSurge, Inc., Rochester, N.Y.

[ * ] Notice: The portion of the term of this patent subsequent to Apr. 30, 2012, has been disclaimed.

[21] Appl. No.: 433,592

[22] Filed: May 3, 1995

Related U.S. Application Data

[60] Continuation of Ser. No. 324,944, Oct. 18, 1994, Pat. No. 5,507,757, which is a division of Ser. No. 876,511, Apr. 30, 1992, Pat. No. 5,368,601.

[51] Int. Cl.⁶ ........................................... A61B 17/00
[52] U.S. Cl. .................... 606/144; 606/139; 606/147; 112/169
[58] Field of Search ................... 606/139, 144, 606/145, 147, 148, 151; 112/169, 80.03

[56] References Cited

U.S. PATENT DOCUMENTS

| | | |
|---|---|---|
| 1,037,864 | 9/1912 | Carlson et al. . |
| 1,449,087 | 3/1923 | Bugbee . |
| 1,822,330 | 9/1931 | Ainslie . |
| 2,108,206 | 2/1938 | Meeker . |
| 2,213,830 | 9/1940 | Anastasi . |
| 2,549,731 | 4/1951 | Wattley . |
| 2,579,192 | 12/1951 | Kohl . |
| 2,601,564 | 7/1952 | Smith . |
| 2,737,954 | 3/1956 | Knapp . |
| 3,090,386 | 5/1963 | Curtis . |
| 3,168,097 | 2/1965 | Dormia . |
| 3,470,875 | 10/1969 | Johnson . |
| 3,496,940 | 2/1970 | Steinman . |
| 3,807,407 | 4/1974 | Schweizer . |
| 3,871,379 | 3/1975 | Clarke . |
| 3,901,244 | 8/1975 | Schweizer . |
| 3,946,740 | 3/1976 | Bassett . |
| 4,103,690 | 8/1978 | Harris . |
| 4,204,541 | 5/1980 | Kapitanov ................... 606/145 |
| 4,493,323 | 1/1985 | Albright et al. . |
| 4,557,265 | 12/1985 | Andersson . |
| 4,597,390 | 7/1986 | Mulhollan et al. . |
| 4,602,635 | 7/1986 | Mulhollan et al. . |
| 4,614,187 | 9/1986 | Mulhollan et al. . |
| 4,621,640 | 11/1986 | Mulhollan et al. . |
| 4,635,638 | 1/1987 | Weintraub et al. . |
| 4,676,243 | 6/1987 | Clayman . |
| 4,827,931 | 5/1989 | Longmore . |
| 4,830,002 | 5/1989 | Semm . |
| 4,836,205 | 6/1989 | Barrett . |
| 4,841,885 | 6/1989 | Santino . |

(List continued on next page.)

FOREIGN PATENT DOCUMENTS

| | | |
|---|---|---|
| 0140557 | 12/1984 | European Pat. Off. . |
| 162960 | 4/1949 | Germany . |
| 4137218 | 2/1993 | Germany . |
| 1093329 | 5/1984 | U.S.S.R. . |
| WO8503858 | 9/1985 | WIPO . |

OTHER PUBLICATIONS

European Search Report for EP 93 10 7072.
Rema Brochure, REMA-Medizintechnik GmbH (believed to be published in 1992).

*Primary Examiner*—Jeffrey A. Schmidt

[57] ABSTRACT

A trocar wound closure device includes an elongated body having a distal end for insertion through a trocar puncture wound, a proximal end, and a first and second retractable needle holders disposed at the distal end of the body. The needle holders are movable between a retracted position and an extended position. An actuator disposed at the proximal end of the body moves the needle holders from the retracted position to the extended position, so that the needle holders can be retracted to allow the device to be inserted through a trocar wound preferably through a cannula inserted into the wound, and extended to position the needles adjacent the wound, to allow the wound to be sutured.

20 Claims, 6 Drawing Sheets

U.S. PATENT DOCUMENTS

| | | |
|---|---|---|
| 4,852,568 | 8/1989 | Kensey . |
| 4,890,615 | 1/1990 | Caspari et al. . |
| 4,898,155 | 2/1990 | Ovil et al. . |
| 4,907,590 | 3/1990 | Wang et al. . |
| 4,923,461 | 5/1990 | Caspari et al. . |
| 4,935,027 | 6/1990 | Yoon . |
| 4,957,498 | 9/1990 | Caspari et al. . |
| 4,963,147 | 10/1990 | Agee et al. . |
| 4,971,067 | 11/1990 | Bolduc et al. . |
| 4,986,825 | 1/1991 | Bays et al. . |
| 5,037,433 | 8/1991 | Wilk et al. . |
| 5,047,039 | 9/1991 | Avant et al. . |
| 5,100,421 | 3/1992 | Christoudias ............ 606/147 |
| 5,109,780 | 5/1992 | Slouf et al. . |
| 5,129,912 | 7/1992 | Noda et al. . |
| 5,152,769 | 10/1992 | Baber . |
| 5,217,471 | 6/1993 | Burkhart . |
| 5,224,948 | 7/1993 | Abe et al. ............ 606/145 |
| 5,318,577 | 6/1994 | Li ............ 606/147 |
| 5,391,174 | 2/1995 | Weston ............ 606/148 |
| 5,403,328 | 4/1995 | Shallman . |

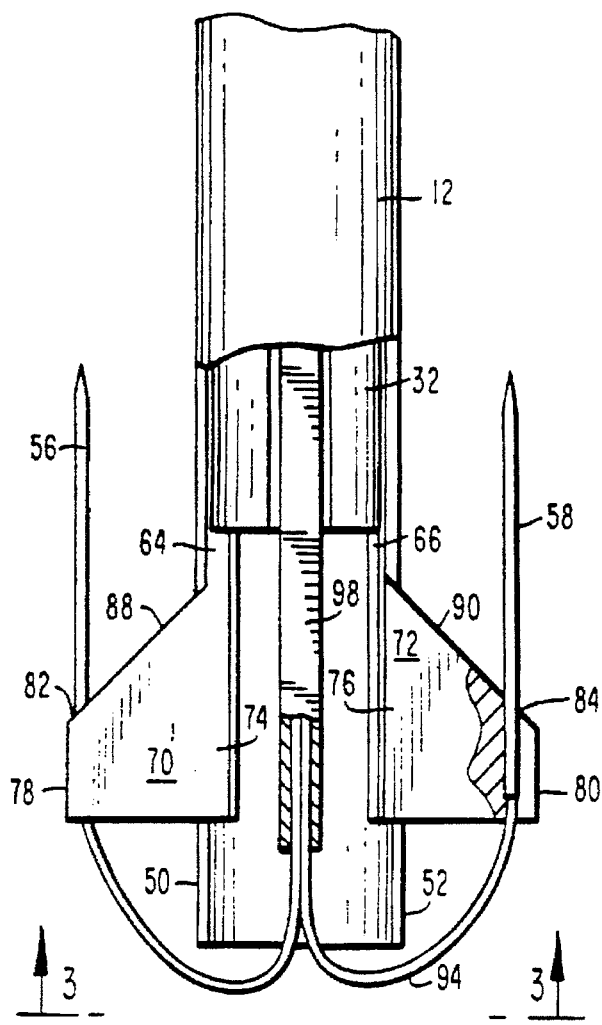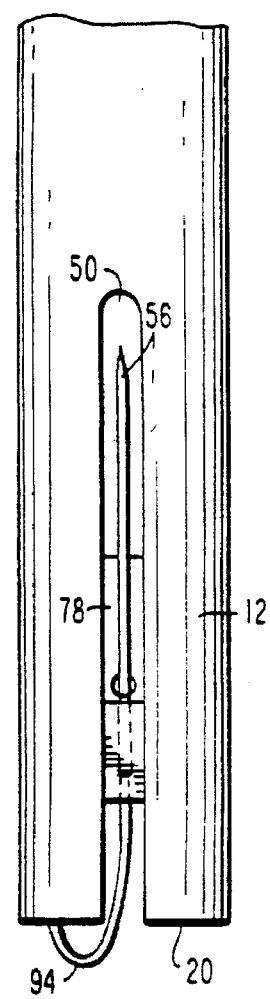
FIG. 4
FIG. 5
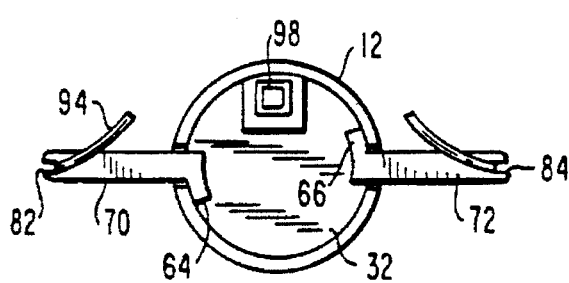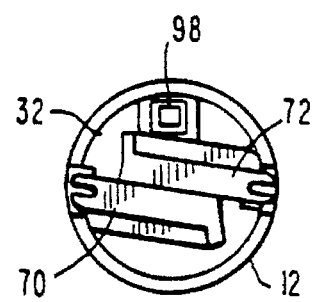
FIG. 6
FIG. 7

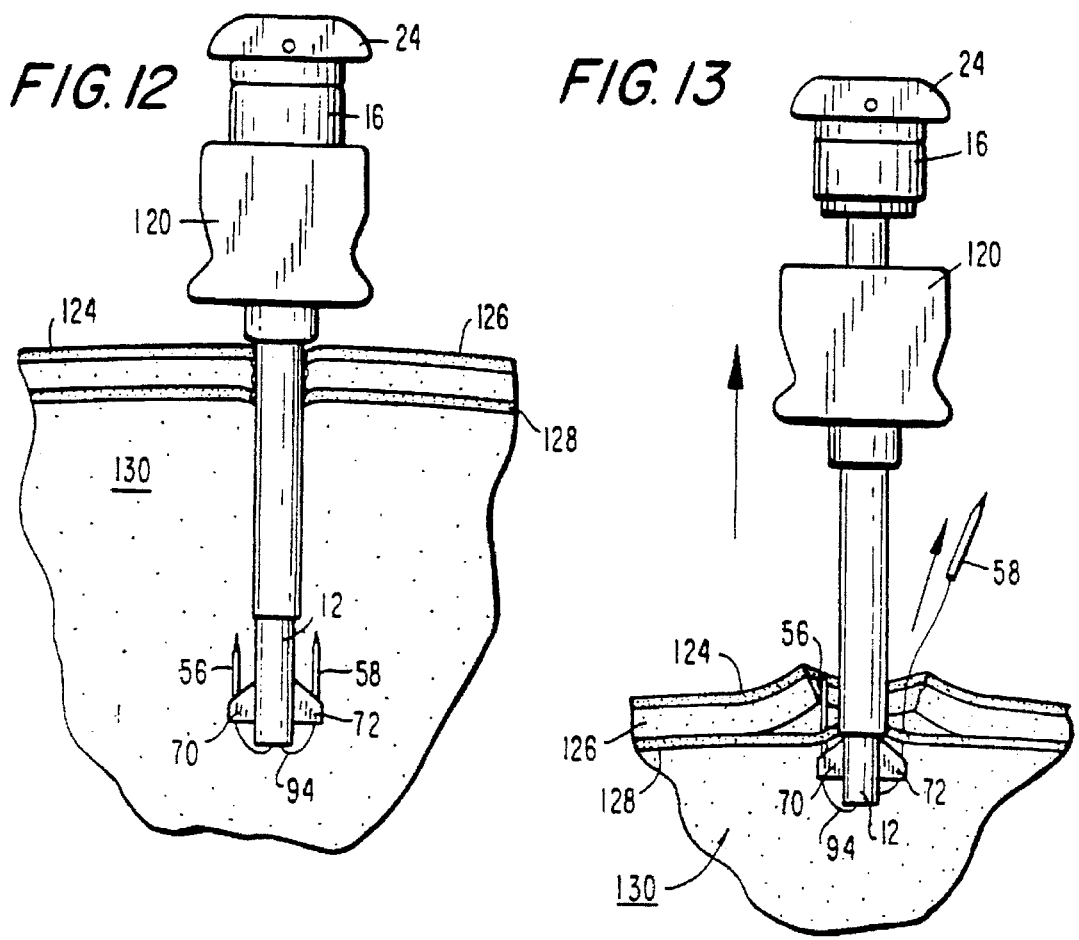
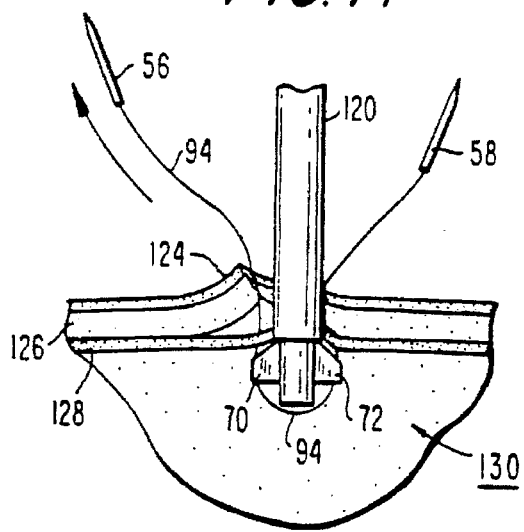
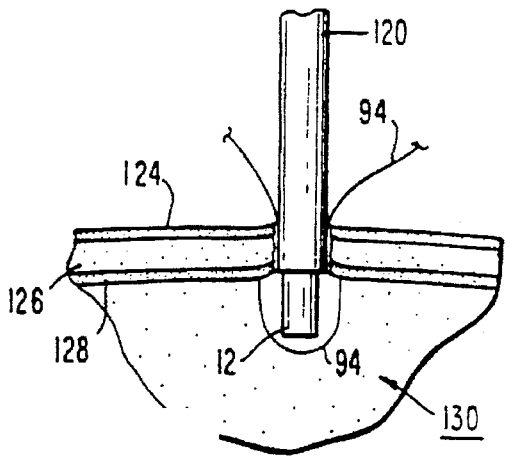

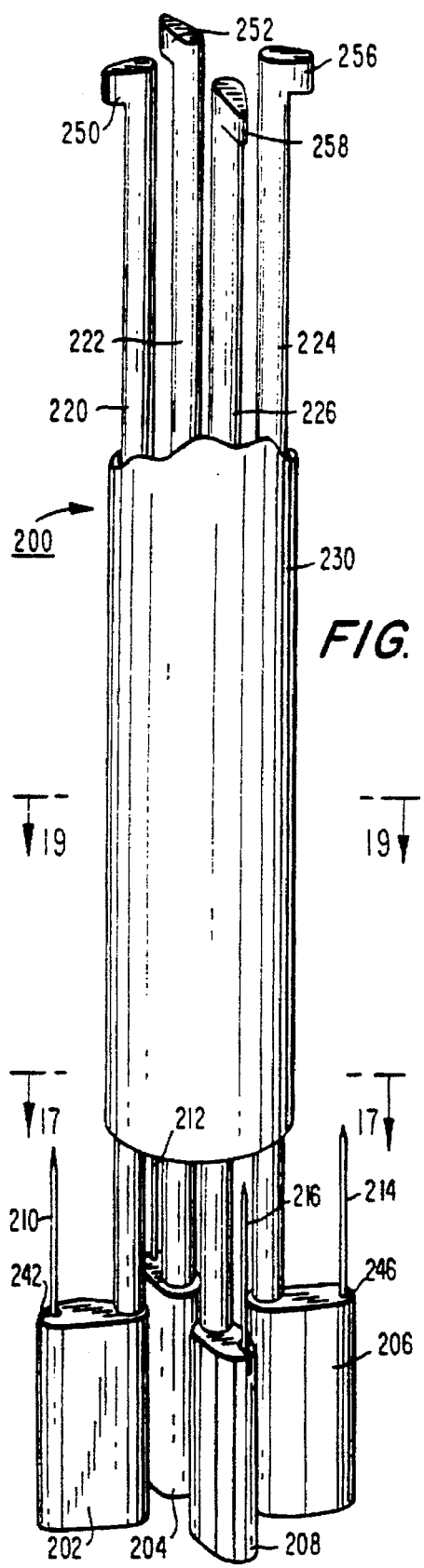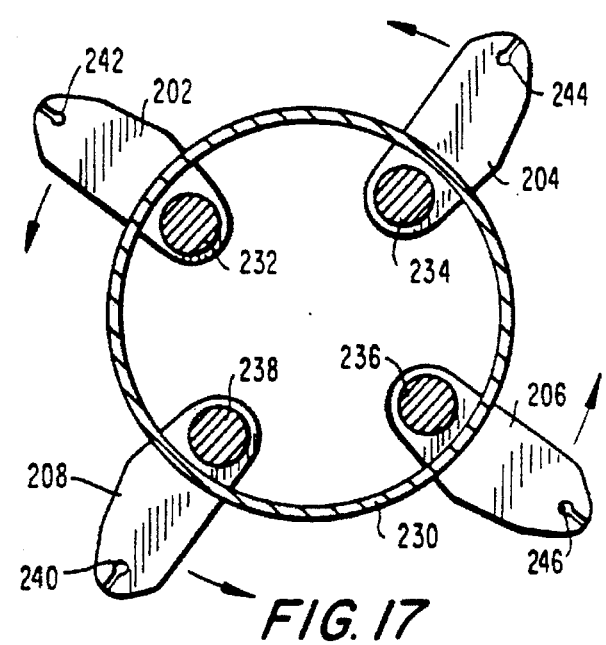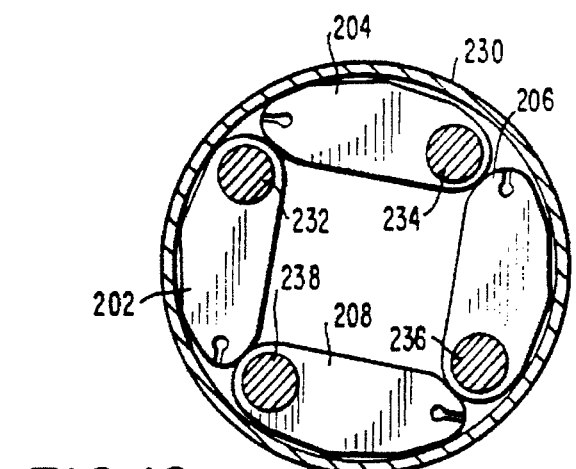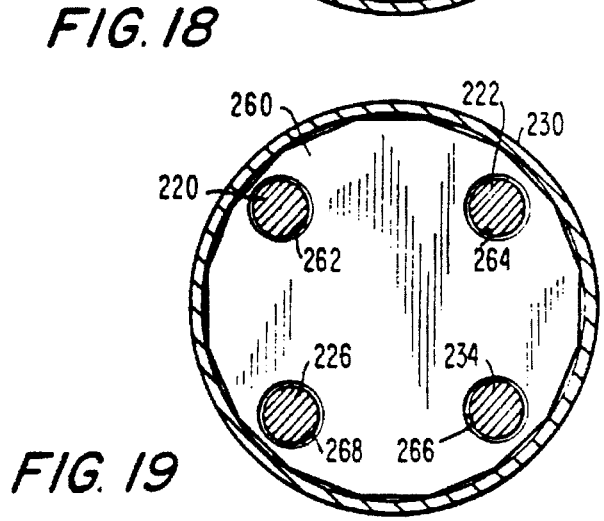

TROCAR WOUND CLOSURE DEVICE

This application is a continuation of application Ser. No. 08/324,944 filed Oct. 18, 1994, now U.S. Pat. No. 5,507,757 which is a divisional application of U.S. application Ser. No. 07/876,511, filed Apr. 30, 1992, now U.S. Pat. No. 5,368,601.

This invention relates generally to devices for facilitating the suturing of trocar puncture wounds, and more particularly to a device that is insertable through a cannula for presenting a pair of needles loaded onto the ends of a suture, in position to close the trocar wound from within an insufflated or otherwise distended abdominal cavity.

Laparoscopic surgery commonly includes the creation of one or more trocar puncture wounds through the anterior abdominal wall for receiving surgical instruments. The structural strength of the abdominal wall is derived mostly from one or more layers of fascia (connective tissue sheets) running parallel to skin and between layers of muscle. The increasing complexity of surgical procedures performed laparoscopically has led to the development and use of larger diameter trocars. Trocars having outside diameters of up to 12 mm. are currently being used, and we anticipate that trocars of up to 20 mm or larger will be used in the future.

While small trocar puncture wounds will often heal satisfactorily without suturing, the wounds created by larger trocars may not. Unless closed properly, larger diameter trocar wounds may allow abdominal contents to herniate into a fascial defect.

Presently, surgeons attempt to suture trocar puncture wounds using conventional hand held needle drivers external to the patient. Because of the limited exposure and the potential for puncturing abdominal organs, conventional needle driving techniques typically place sutures only through the outer layers of fascia. These manual techniques are often further compromised by patient obesity and other factors.

Accordingly, there is a need for an improved method of closing trocar puncture wounds to minimize the risk of puncture site herniation or other undesirable side effects of known trocar wound closure techniques.

Briefly stated, a trocar wound closure device according to this invention includes an elongated body having a distal end for insertion through a trocar puncture wound, a proximal end, and a first and second retractable needle holders disposed at the distal end of the body. The needle holders are movable between a retracted position and an extended position. An actuator disposed at the proximal end of the body moves the needle holders from the retracted position to the extended position, so that the needle holders can be retracted to allow the device to be inserted through a trocar wound preferably through a cannula inserted into the wound, and extended to position the needles adjacent the wound, to allow the wound to be sutured.

In accordance with another aspect of this invention, the elongated body is a tubular body, and the needle holders are elongated cantilevered arms fixed at the proximal end, and free at the distal end.

In accordance with a further aspect of this invention, the retractable needle holders are movable from a retracted position within the tubular body to an extended position outside the tubular body.

In accordance with a still further aspect of this invention, the needle holders have tapered retracting edges for causing the needle holders to retract as the wound closure device is withdrawn from a trocar wound, especially through a cannula.

In accordance with a still further aspect of this invention, the actuator comprises a plunger movable within the tubular body from an extended position to a depressed position, for engaging and moving the cantilevered arms outward as the plunger is depressed, and moving the needle holders from the retracted position to the extended position, respectively.

In accordance with a still further embodiment of this invention, the needle holders are needle plates slidably mounted in the elongated body, with needle holding edges oriented generally parallel to the body.

In accordance with another aspect of this invention, the body includes a tube for carrying a suture within the body.

While the novel aspects of this invention are set forth with particularity in the appended claims, the invention itself, together with further objects and advantages thereof, may be more readily comprehended by reference to the following detailed description of a presently preferred embodiment of the invention, taken in conjunction with the following drawings, in which:

FIG. 4 is an enlarged segmental view of the distal end of the trocar wound closure device of FIG. 1, shown partly in section, and loaded with a suture;

FIG. 5 is a side elevation of the distal end of the trocar wound closure device shown in FIG. 4;

FIG. 6 is a bottom plan view of the distal end of the trocar wound closure device of FIG. 4 showing the needle holders in the extended position; and FIG. 7 is a bottom plan view similar to FIG. 6, but showing the needle holders in the retracted position with the suture and needles omitted for clarity;

FIG. 12 is a side elevational view, partly in section, showing the trocar wound closure device fully inserted into the cannula with the needle holders extended;

FIG. 13 is a side elevational view, partly in section, showing the process of withdrawing the wound closure device and cannula to cause the needles to pierce the peritoneal wall;

FIG. 14 is a fragmentary side elevational view showing the distal end of the trocar wound closure device as both sides of the the suture are pulled through the peritoneal wall;

FIG. 15 is a fragmentary side elevational view showing the trocar wound closure device with the needle holders retracted in preparation for withdrawal from the trocar puncture wound site;

FIG. 16 is a perspective view of an alternative embodiment of the distal end of a trocar wound closure device;

FIG. 17 is a section thereof taken along lines 17—17 of FIG. 16 showing the needle Molders rotated to an extended position;

FIG. 18 is a section taken along the same line showing the needle holders rotated to a retracted position; and FIG. 19 is a section taken along line 19—19 of FIG. 16 showing the distal end of the alternative embodiment of the trocar wound closure device.

Figure 1:
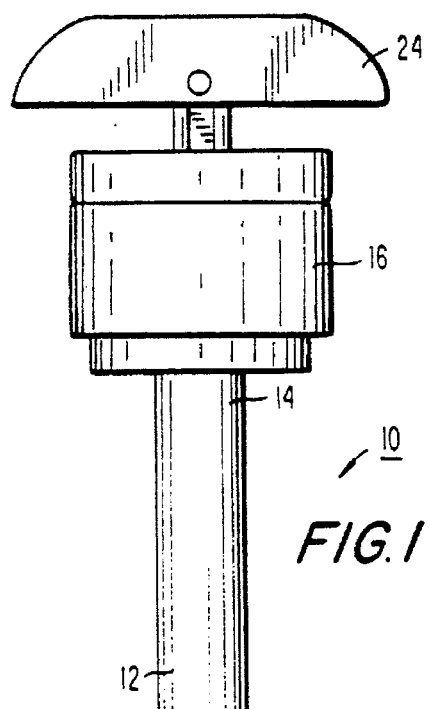
FIG. 1 is a side elevational view of a trocar wound closure device in accordance with this invention.
Figure 2:
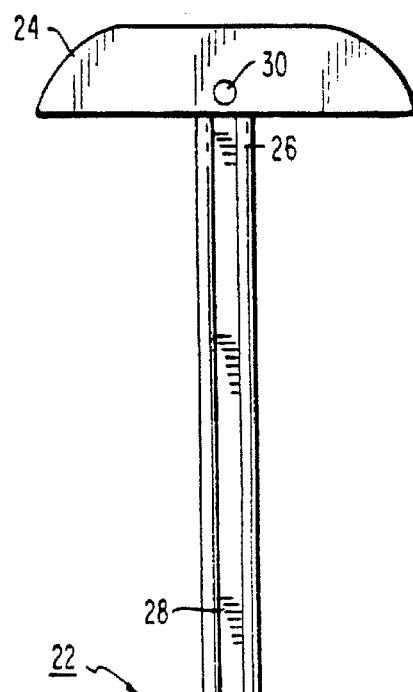
FIG. 2 is a side elevation of the plunger of the trocar wound closure device of FIG. 1.
Figure 3:
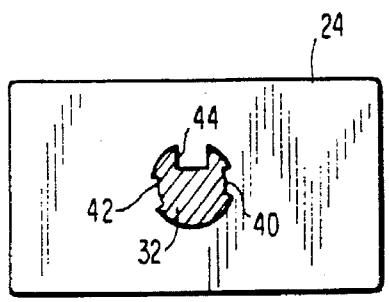
FIG. 3 is a bottom plan view of the plunger of FIG. 2.

In a presently preferred embodiment of the invention as shown in FIG. 1, the trocar wound closure device 10 includes an elongated tubular, preferably cylindrical, body 12 having a proximal end 14 inserted into a housing block 16, preferably formed from a moldable or machinable plastic, soft metal or the like, and a distal end 20. A plunger 22 having a handle 24 attached thereto at one end 26 is slidably received within the tubular body 12. The plunger 22 is shown in a side elevation in FIG. 3, and a bottom plan view of the plunger is shown in FIG. 2. The plunger 22 includes the handle 24 already described, and an elongated shaft 28 attached to the handle by conventional fasteners, such as a screw or rivet 30.

An actuating element 32 is attached to the distal end 34 of the elongated shaft 28. The actuating element 32 is preferably machined or molded from a low coefficient of friction plastic material such as delrin or the like. It is generally cylindrical in cross section, and has three longitudinally extending notches 40, 42, 44 formed therein, spaced radially around the periphery of the actuating element 32. A first shallow notch 40 and a second shallow notch 42 are adapted to engage first and second needle drivers as will be shown and described in more detail later. A deeper notch 44 receives a suture holder.

The distal end 20 of the trocar wound closure device 10 is shown in more detail in FIG. 4, which is partly broken away and sectioned for convenience. First and second elongated slots 50 and 52 are formed in the distal end 20 of the tubular body 12, as can be seen also in FIGS. 5, 6, and 7. The slots 50 and 52 extend from the distal end 20 of the body 12 towards the proximal end 14 a distance sufficient to allow first and second needles 56 and 58 to be retracted laterally into the body through the slots 50 and 52.

The needles 56 and 58 are carried by needle drivers having first and second elongated resilient bars 64 and 66. The bars have first and second fin shaped needle carriers 70 and 72 attached at the distal ends of the bars 64 and 66. Each of the needle holders has a long side 74, 76 attached to the respective distal end of its bar, and a remote shorter side 78, 80 having a needle carrying groove 82, 84 formed therein. The top sides 88, 90 of the needle holders are preferably tapered from the long sides to the short sides to assist the needle holders in being retracted into the tubular body 12, as will be described in more detail later.

A suture 94, armed at its ends with needles 56, 58, is carried by the device, as seen best in FIG. 4. The needles 56, 58 are mounted in the needle carrying grooves 82 and 84 in the needle carriers 70, 72, and the suture 94 is loaded into a suture receiving tube 98 that extends upwardly inside the tubular body 12. As best seen in FIG. 6, the needle carriers 70 and 72 and the tube are received in the slots 40, 42 of the actuating member 32. The deep slot 44 is preferably sized to surround the suture holding tube without engaging it, while the shallow slots 40 and 42 are sized and shaped to engage the resilient bars 64, 66 carrying the needle carriers 70 and 72.

When the plunger 22 is fully depressed, the actuating member 32 moves within the tubular body 12 towards the distal end 20 of the trocar wound closure device 10, and pushes the needle carriers 70, 72 to an extended position as shown in FIG. 6. When the plunger 22 is withdrawn, the actuating member 32 slides towards the proximal end 14 of the device, and the resilient bars 64, 66 move into the tubular body to withdraw the needle carriers 70, 72 into the body of the trocar wound closure device, as shown in FIG. 7, from which the needles and suture are omitted for clarity.

Figure 8:
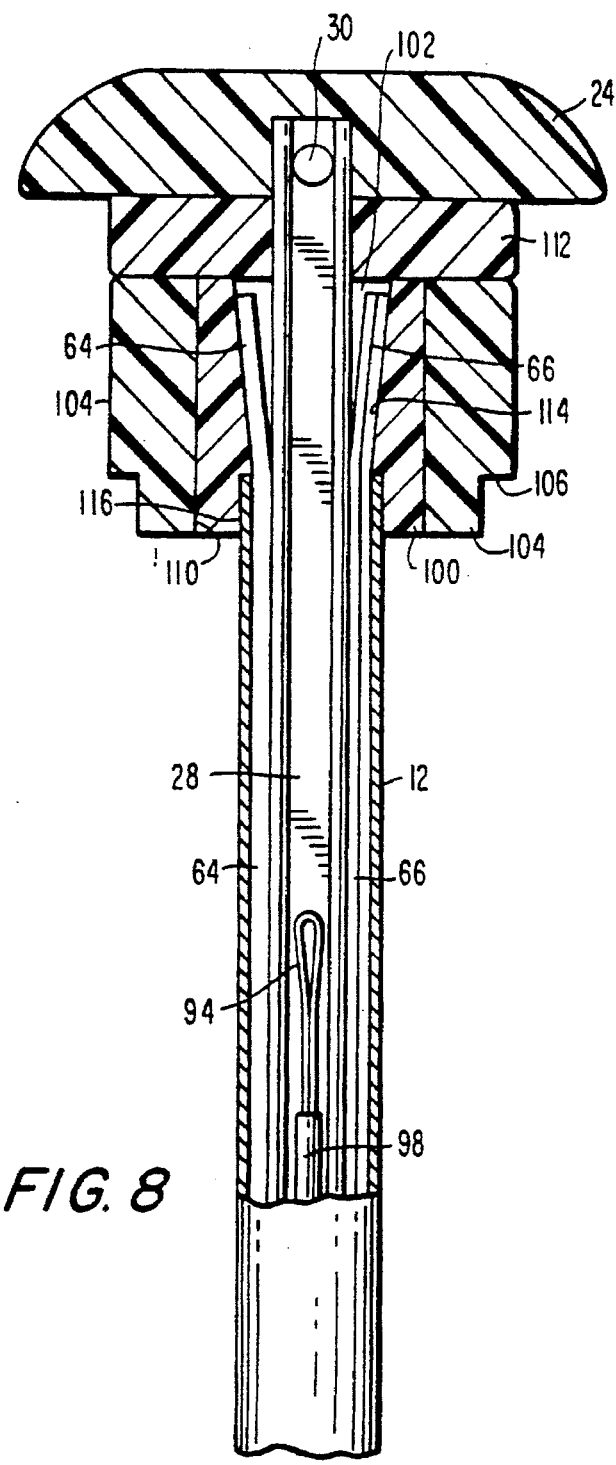
FIG. 8 is an enlarged view of the proximal end of the trocar wound closure device, shown partly in section, with the plunger fully depressed.
Figure 9:
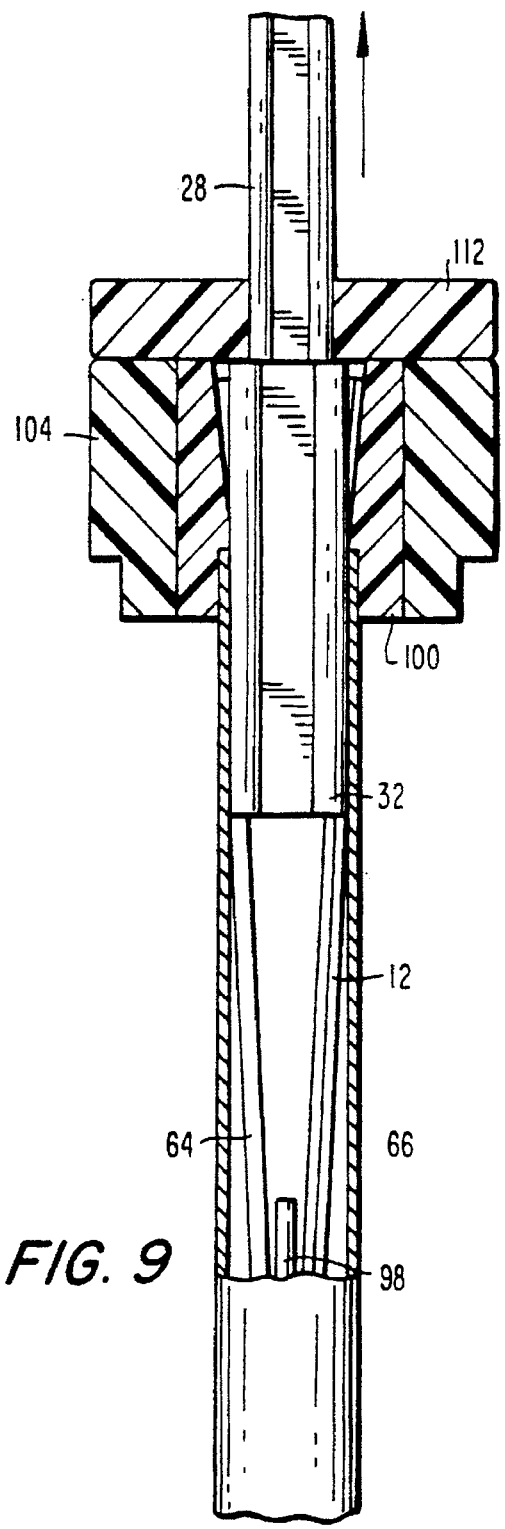
FIG. 9 is an enlarged side elevational view of the proximal end of the trocar wound closure device similar to that shown in FIG. 8, but with the plunger extended.

These same two conditions are shown in the section views of the proximal end of the device illustrated at FIGS. 8 and 9. FIG. 8 shows the plunger 22 fully depressed, and FIG. 9 shows the plunger 22 fully withdrawn. The housing block 16 is formed from three elements. An inner carrier member 100, preferably cylindrical in configuration and having a through bore therein is mounted within an outer generally rectangular member 104 having a peripheral notch 106 for receiving the top of a cannula and a bore 110 for receiving the inner carrier 100. A flat rectangular cap 112 closes one end of the member, and includes a central bore 114 for receiving the elongated shaft 28 of the plunger 22 therethrough.

The tubular body member 12 is mounted in a slightly enlarged annular recess 116 in the through bore 102 of the inner member 100. The through bore 102 is tapered from a small diameter at its distal end towards a larger diameter at its proximal end. The proximal ends of the resilient bars 64, 66 are attached at radially opposed positions on the inner surface of the tapered portion of the through bore 102. Preferably, the bars 64 and 66 are made from spring steel or a similar resilient material, and are formed so that they naturally assume the position as shown in FIG. 9, to retract the needle carriers 70 and 72 to the FIG. 7 position, withdrawn into the interior of the distal end 20 of the tubular body 12 when the actuating member 32 is withdrawn to the position shown in FIG. 9.

The shallow botches 40, 42 of the actuating element 32 engage the inner surfaces of the bars 64 and 66, as will be recalled from FIG. 6. As the plunger 22 is depressed, the actuating element 32 progressively urges the bars 64 and 66 from their natural position to a position adjacent the inner surface of the tubular body 12 as shown in FIGS. 4, 6 and 8, and at the same time urges the needle carriers 70, 72 to an extended position outside the distal end 20 of the tubular body 12. The upper end of the suture holding tube 98 is also visible in FIGS. 8 and 9. As shown in FIG. 8, a bight formed in the suture 94 may extend slightly beyond the upper end of the suture holder 98, shown shorter than actual size for clarity. As shown in FIG. 9, which in this aspect is meant to represent the wound closure device after the suture has been withdrawn through the peritoneal wall, the bight at the center of the suture 94 has disappeared to show that the suture has been withdrawn.

Figure 10:
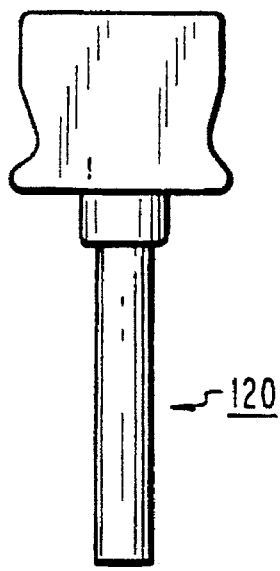
FIG. 10 is a simplified side elevational view of a cannula for use with a trocar wound closure device in accordance with this invention.

While the trocar wound closure device of this invention may be inserted directly into a trocar wound site, it is conventional in laparoscopic procedures to employ a cannula 120 as shown in FIG. 10 during a procedure. The trocar wound closure device of this invention is particularly adapted to be used with the cannula 110 in place at the wound site.

Figure 11:
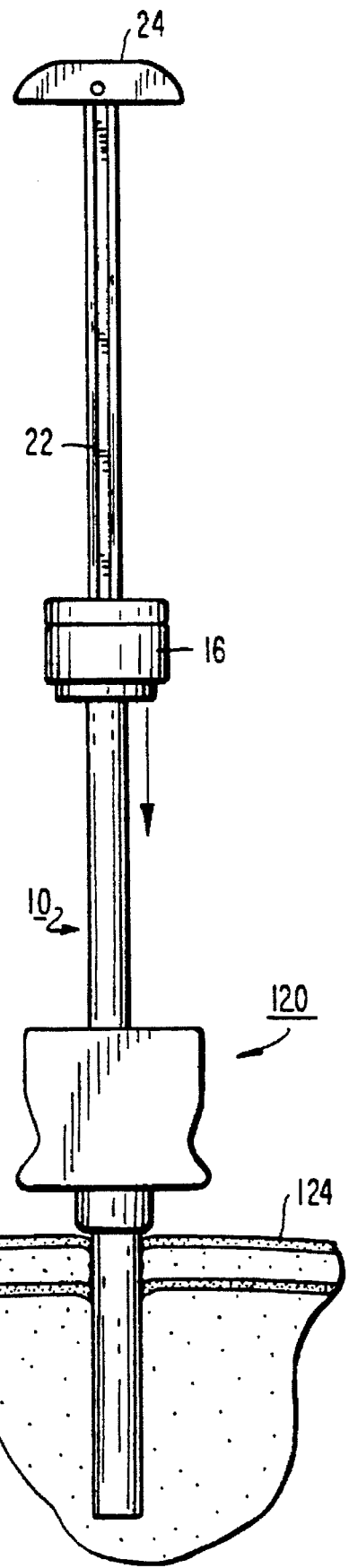
FIG. 11 is a side elevational view, partly in section, showing the cannula of FIG. 10 inserted through a trochar wound into a peritoneal cavity with the trocar wound closure device of this invention in the process of being inserted into the cannula.

FIG. 11 shows the cannula 120 of FIG. 10 inserted through a trocar puncture wound. The cannula 110 passes through the skin 124, a fat, layer 126 and the fascia 128 into the peritoneal cavity 130.

The invention may be more fully understood by reviewing the manner in which the invention is used to place a suture at a trocar puncture wound site. The suture 94 is armed at each end with a needle 56, 58. As shown in FIGS. 4 and 8, the center of the suture is stored inside the tube 98 within trocar wound closure device, to keep it from becoming tangled. The needles are mounted in the grooves 82 and 84 of the two needle carriers 70 and 72, as shown in FIG. 4, with the sharp ends of the needles pointing towards the proximal end 14 of the trocar wound closure device 10. The suture 94 extends from the distal end of each needle into the body of the trocar wound closure device. The needle carriers 70, 72 are retracted inside the tubular body 12 of the trocar wound closure device to the position shown in FIG. 7, so that the outside diameter of the loaded trocar wound closure device is less than the inside diameter of the trocar puncture wound or of the cannula 120.

The trocar wound closure device 10, with the needle carriers retracted, is inserted through the cannula into the peritoneal cavity 130, with the plunger 22 retracted as shown in FIG. 11. The plunger 22 is depressed to extend the needle carriers 70, 72 and position the needles 56 and 58 adjacent to but outside the edges of the puncture wound, and in position to puncture the fascia 128 adjacent the wound site as shown in FIG. 12. The trocar wound closure device 10 and the cannula 120 are simultaneously pulled outwardly with respect to the cavity 130, and the needles pass through the fascia 128 as shown in FIG. 13. The skin 124 and intermediate layer of fat 126 are grasped and retracted from the trocar wound site. The needles 56, 58 are located and pulled only through the fascia and muscle layers, with conventional needle drivers or the like as shown in FIG. 14. As the needles and then the suture are pulled through the fascia, the remainder of the suture is controllably released from the suture tube 98 as in FIG. 14. The plunger 22 is first withdrawn to the extended position, prior to withdrwing the trocar wound closure device 10 from the cannula 120. The trocar wound closure device is then retracted from the cannula. The taper of the needle carriers will cause retraction of the needle carriers into the body of the trocar wound closure device as the device is withdraw as shown in FIG. 15. After the cannula 120 is withdrawn from the wound a surgical knot is placed over the fascial wound site, thereby closing the wound through the fascia, beneath the fat and skin. The ends of suture are cut. The outer layers of skin and fat are positioned anatomically over the fascial closure, and closed or covered in a conventional manner.

An alternative embodiment of the trocar wound closure device of this invention is shown in FIGS. 16, 17, 18, and 19. Only the distal end of the device is illustrated in the figures, it being understood that any conventional actuating means as will occur to those skilled in the art may be used. The device shown in these figures includes four needle carriers 202, 204, 206, and 208 rather than two, and is especially suitable for closing large trocar wounds. Four needles 210, 212, 214 and 216 are mounted at the ends of rotatable tubes 220, 222, 224, and 226, carried within the tubular body member 230 of the trocar wound closure device 200. The suture(s) can be stored within one or more of these tubes. The needle holders are elongated and generally oblong in configuration, and each includes an enlarged recess 232, 234, 236, 238 for receiving the end of its respective rotatable tube, and a small recess and slot 240, 242, 244, 246 for receiving a suture armed with a needle. The peripheries of the needle holders are configured so that when rotated to a retracted position as shown in FIG. 18, they will fit within the inside of the tubular body 230. At their upper ends, the rotatable tubes are provided with cam shaped actuating members 250, 252, 256 and 258, to allow the rods to be rotated to move the needle holders from an extended position, as shown in FIG. 17, to a retracted position as shown in FIG. 18. Preferably, at least one spacer 260 as shown in FIG. 19 is provided within the tubular body member for maintaining the rotatable rods in a spaced apart configuration, while allowing them to turn freely within apertures 262, 264, 266 and 268 in the spacer.

While the invention has been shown and described in connection with a presently preferred embodiment thereof, those skilled in the art will recognize that certain modifications and changes may be made therein without departing from the true spirit and scope of the invention, which accordingly is intended to be defined solely by the appended claims.

What is claimed is:

1. A trocar wound closure device, which comprises:
   a) an elongated body;
   b) first and second needle holders operably disposed at a distal end of the elongated body and defining first and second needle holding portions to hold first and second needles therein, respectively, the first and second needle holders bring movable from a retracted position to an extended position, wherein in the extended position of the needle holders, the first and second needle holding portions are spaced a predetermined distance from the central longitudinal axis of the elongated body; and
   c) an actuator operatively associated with the first and second needle holders to effect movement thereof from the first position to the second position.

2. A trocar wound closure device according to claim 1, wherein each the needle holding portions defines a recess dimensioned to receive the respective needle.

3. A trocar wound closure device, according to claim 1, wherein the first and second needle holders are movable radially between the retracted and extended positions.

4. A trocar wound closure device, according to claim 1, wherein the actuator includes a camming surface which cams the first and second needle holders from the retracted position to the extended position upon movement of the actuator in a predetermined direction.

5. A trocar wound closure device, according to claim 4, wherein the actuator is longitudinally movable to effect movement of the first and second needle holders between the retracted and extended positions.

6. A trocar wound closure device, according to claim 1, wherein distal movement of the actuator causes the first and second needle holders to move toward the extended position.

7. A trocar wound closure device, according to claim 1, wherein the first and second needle holders are biased toward the retracted position.

8. A trocar wound closure device which comprises:
   a) an elongated body having a longitudinal axis, a substantially straight distal end portion, and an opening formed in the distal end portion, the opening extending less than the entire length of the elongated body;
   b) a needle holder operatively associated with the elongated body and movable between a first position substantially within the opening and a second position substantially outside the opening, the needle holder including a needle receiving portion; and
   c) a needle supported within the needle holder, wherein movement of the needle holder to the second position moves the needle to a position outside the opening wherein the needle is retained in the needle receiving portion when the needle holder is positioned in either the first or second positions.

9. A trocar wound closure device, according to claim 8, wherein the needle is removably supported in the needle holder.

10. A trocar wound closure device, according to claim 8, wherein the needle holder is movable radially between the first and second positions.

11. A trocar wound closure device, according to claim 8, which further comprises an actuator operatively associated with the needle holder to effect movement thereof from the first position to the second position.

12. A trocar wound closure device, according to claim 11, wherein the actuator includes a camming surface which cams the needle holder from the first position to the second position upon movement of the actuator in a predetermined direction.

13. A trocar wound closure device, according to claim 11, wherein distal movement of the actuator causes the needle holder to move toward the second position.

14. A trocar wound closure device, according to claim 11, wherein the needle holder is biased toward the first position.

15. A trocar wound closure device, which comprises:
   a) an elongated body;
   b) a needle holder disposed near a distal end of the elongated body and having a needle receiving portion formed thereon and being rotatably deployable such that the needle receiving portion is movable between a retracted position and an extended position;
   c) a needle supported in the needle receiving portion and having a tapered end portion, the needle being movable between a first position wherein the tapered end portion is disposed substantially within the elongated body and a second position wherein the tapered end is spaced a distance from the elongated body such that the needle is retained in the needle receiving portion when the needle holder is positioned in either the first or second positions; and
   d) an actuator operatively connected to the needle holder and rotatable relative to the elongated body to effect movement of the needle receiving portion from the retracted position to the extended position.

16. A trocar wound closure device, according to claim 15 wherein the needle holder is pivotably rotatable.

17. A trocar wound closure device, according to claim 15, wherein when the needle receiving portion is in the extended position, the needle is oriented such that the tapered end portion thereof is directed generally towards a proximal end of the device.

18. A trocar wound closure device, according to claim 15, wherein the actuator includes an indicating portion disposed near a proximal end which provides indication to a user of the relative positioning of the needle holder.

19. A trocar wound closure device, which comprises:
   a) an elongated body;
   b) a plurality of needle holders operatively associated with the elongated body each needle holder having a needle receiving portion formed thereon and being rotatably deployable such that the needle receiving portion is movable between a retracted position and an extended position;
   c) a needle supported in the needle receiving portion of at least one of the plurality of needle holders; and
   d) an actuator operatively connected to at least one of the plurality of needle holders and rotatable relative to the elongated body to effect movement of the needle receiving portion from the retracted position to the extended position.

20. A trocar wound closure device, according to claim 19, which further comprises a separate actuator for each of the plurality of needle holders wherein the separated actuators are operatively connected to the respective needle holders such that each needle holder is individually actuatable.

* * * * *